(12) United States Patent
Tewari

(10) Patent No.: US 8,241,310 B2
(45) Date of Patent: Aug. 14, 2012

(54) URETHRAL CATHETERLESS RADICAL PROSTATECTOMY

(75) Inventor: Ashutosh K. Tewari, Valhalla, NY (US)

(73) Assignee: Cornell University, Ithaca, NY (US)

( * ) Notice: Subject to any disclaimer, the term of this patent is extended or adjusted under 35 U.S.C. 154(b) by 610 days.

(21) Appl. No.: 12/355,807

(22) Filed: Jan. 19, 2009

(65) Prior Publication Data

US 2010/0185154 A1 Jul. 22, 2010

(51) Int. Cl.
*A61B 17/08* (2006.01)
(52) U.S. Cl. .................. 606/153; 606/151; 606/157
(58) Field of Classification Search .......... 604/175, 604/96.01; 606/151, 153, 157, 213; 600/29–32, 600/39, 40
See application file for complete search history.

(56) References Cited

U.S. PATENT DOCUMENTS

| | | | | |
|---|---|---|---|---|
| 5,019,032 A | * | 5/1991 | Robertson | 600/29 |
| 5,232,443 A | * | 8/1993 | Leach | 604/517 |
| 5,483,976 A | * | 1/1996 | McLaughlin et al. | 128/885 |
| 6,299,598 B1 | | 10/2001 | Bander | |
| 6,440,060 B1 | * | 8/2002 | Latour, Jr. | 600/30 |
| 7,897,167 B2 | * | 3/2011 | Armstrong et al. | 424/426 |
| 7,909,799 B2 | * | 3/2011 | Frassica | 604/165.04 |
| 2003/0229264 A1 | * | 12/2003 | Connors et al. | 600/29 |
| 2004/0143343 A1 | * | 7/2004 | Grocela | 623/23.66 |
| 2007/0191768 A1 | * | 8/2007 | Kolb | 604/104 |

OTHER PUBLICATIONS

Ates, et al. "A New Postoperative Predictor of Time to Urinary Continence after Laparoscopic Radical Prostatectomy: The Urine Loss Ratio," European Urology. 2007, vol. 52; pp. 178-185.

Tewari, et al. "Catheter-less robotic radical prostatectomy using a custom-made synchronous anastomotic splint and vesical urinary diversion device: report of the initial series and perioperative outcomes," BJU International. 2008, vol. 102; pp. 1000-1004.
Branagan, et al. "Published Evidence Favors the Use of Suprapubic Catheters in Pelvic Colorectal Surgery," Dis Colon Rectum. 2002, vol. 45, No. 8; pp. 1104-1108.
Dinneen, et al. "Urethral Strictures and Aortic Surgery. Suprapubic rather than Urethral Catheters," Eur J. Vasc Surg. 1990, vol. 4; pp. 535-538.
Krisman, et al. "Suprapublic Bladder Drainage Following Anterior Vaginal Wall Repair," Canad. Med. Ass. J. 1969, vol. 101; pp. 164-166.
Menon, et al. "Vattikuti Institute Prostatectomy: Contemporary Technique and Analysis of Results," European Urology. 2007, vol. 51, pp. 648-658.
Menon, et al. "The technique of apical dissection of the prostate and urethrovesical anastomosis in robotic radical prostatectomy," BJU International. 2004, vol. 93; pp. 715-719.
Niel-Weise, et al. "Urinary catheter policies for short-term bladder drainage in adults (Review)," The Cochrane Collaboration. 2009, vol. 3; pp. 1-48.

(Continued)

*Primary Examiner* — Corrine M McDermott
*Assistant Examiner* — Alexander Orkin
(74) *Attorney, Agent, or Firm* — Michael A. Davitz

(57) ABSTRACT

A method and device for facilitating the anastomotic healing of a patient after a radical prostatectomy surgical procedure, without a urethral catheter, comprising the steps of performing a radical prostatectomy, fixedly positioning a splinting element between the urethra and the bladder, across the urethral opening, placing the splinting element during the performing of the radical prostatectomy and prior to surgical closure. The fixed positioning is effected from a position within the bladder with anchoring the splinting element in position relative to the interior of the bladder, setting a separate urine drainage tube, and removing the splinting element, after anastomotic healing, with a retrieval element on the splinting element or with dissolving of the splinting element.

10 Claims, 1 Drawing Sheet

OTHER PUBLICATIONS

Patel, et al. "Robotic radical prostatectomy: outcomes of 500 cases," BJU International. 2007, vol. 99; pp. 1109-1112.

Souto, et al. "Experience with Early Catheter Removal after Radical Retropubic Prostatectomy," The Journal of Urology. 2000, vol. 163; pp. 865-866.

Tewari, et al. "Total reconstruction of the vesico-urethral junction," BJU International. 2008, vol. 101; pp. 871-877.

Tewari, et al. "Anatomic Restoration Technique of Continence Mechanism and Preservation of Puboprostatic Collar: A Novel Modification to Achieve Early Urinary Continence in Men Undergoing Robotic Prostatectomy," Urology. 2007, vol. 69, No. 4; pp. 726-731.

Tewari, et al. "Cancer control and the preservation of neurovascular tissue: how to meet competing goals during robotic radical prostatectomy," BJU International. 2008, vol. 101; pp. 1013-1019.

Tewari, et al. "The proximal neurovascular plate and the tri-zonal neural architecture around the prostate gland: importance in the athermal robotic technique of nerve-sparing prostatectomy," BJU International. 2006, vol. 98; pp. 314-323.

* cited by examiner

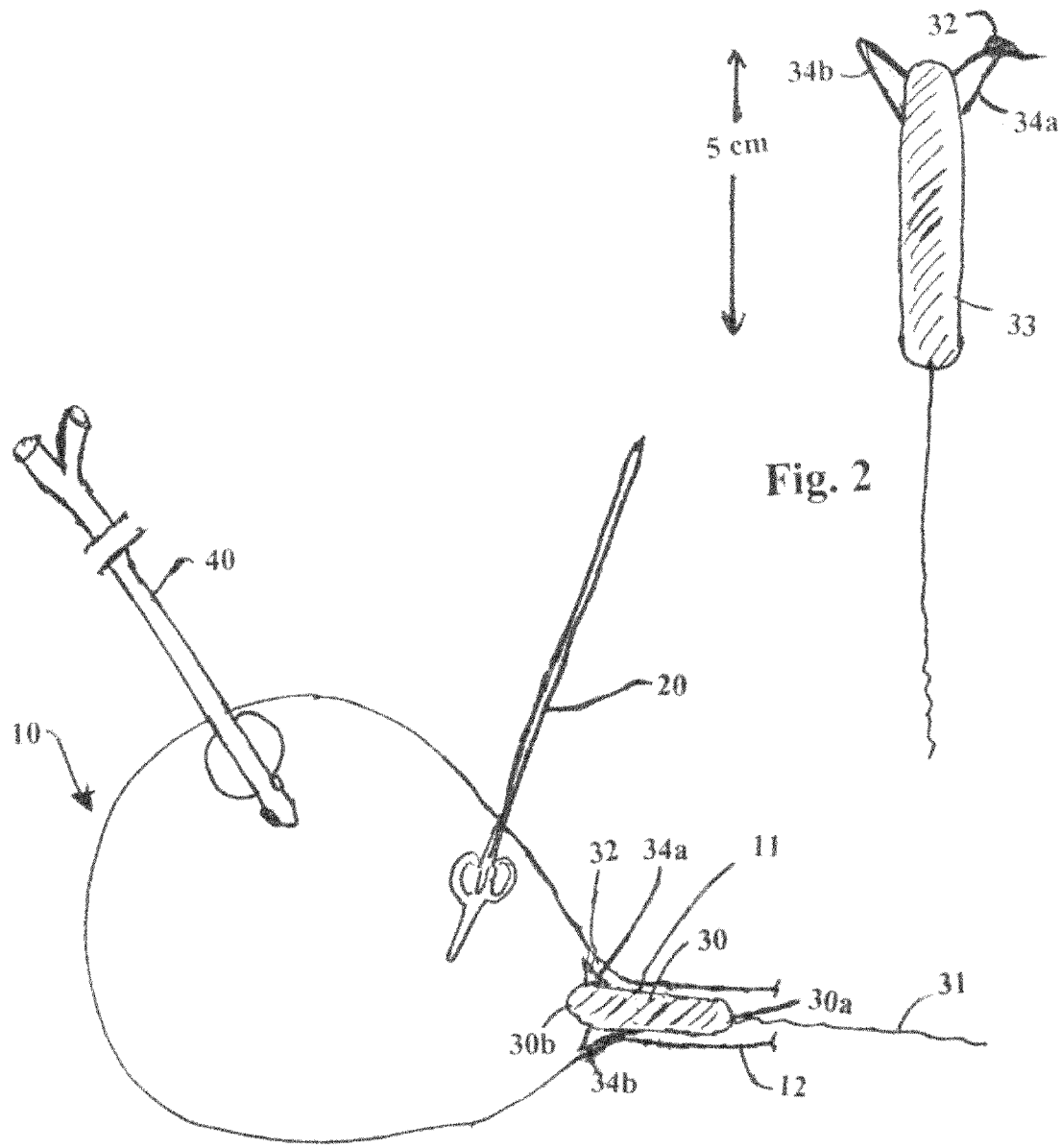

URETHRAL CATHETERLESS RADICAL PROSTATECTOMY

FIELD OF THE INVENTION

This invention relates to procedures for performing radical prostatectomy and post operative anastomotic healing and particularly to splinting procedures not involving urethral catheters in robotic procedures.

BACKGROUND OF THE INVENTION

Radical prostatectomy involves a rejoining of bladder to urethra and a catheter for 1-3 weeks. If the new joint is not splinted with a catheter it will close due to scarring. Additionally urine needs an outlet (provided by the catheter).

Radical prostatectomy is the most common oncological procedure performed by urologists and leaving an indwelling urethral catheter is considered mandatory after open or laparoscopic radical prostatectomy to allow anastomotic healing. The duration of catheterization averages about 5-7 days in most minimally invasive series. However, urinary catheterization is a source of infection, discomfort, anxiety and embarrassment to the patient undergoing radical prostatectomy. Definitive morbidity, such as discomfort, bacteriuria and urethral stricture, is also directly associated with the time a catheter is left in place after surgery.

There have been no published clinical trials of radical prostatectomy performed without a urethral catheter. In gynecological and vascular procedures, a suprapubic catheter has been shown to be better than a urethral catheter. In a review of 5 randomized control trials comparing suprapubic catheter and urethral catheter in colorectal surgery it was demonstrated that patients with a suprapubic catheter experienced less pain and discomfort than the urethral group and the suprapubic catheter was preferred by those patients who had experience with both. In addition the ability to attempt normal voiding is enhanced with the later. There is also evidence to suggest that suprapubic catheters are better than indwelling urethral catheters in term of bacteriuria, need for re-catheterization and discomfort. The risk of developing bacteriuria from a catheter increases by 3-6% per day with the urethral catheter. This would mean that by 7 to 10 days the risk would increase to 50%.

Suprapubic catheterization is a standard procedure performed routinely in urological practice for other indications. The anticipated adverse events include blocked catheter, slippage and displacement of catheter. Displacement is a rare event and can be remedied simply by placing a urethral catheter with no consequences to the final result.

Other problems associated with indwelling urethral catheters include encrustation of the catheter, bladder spasms resulting in urinary leakage, hematuria and urethritis. A suprapubic tube is more patient-friendly, with no risk of urethral damage. Bladder spasms occur less frequently and suprapubic tubes are generally more sanitary. They may also cause fewer urinary tract infections than standard urethral catheters. Thus the benefits of the suprapubic route are reduced infection, control and monitoring of return of normal voiding, reduced need to recatheterize, avoidance of possible urethral damage and improved patient satisfaction. Drainage tubes using the suprapubic route however have a major drawback since this alternative to a urethral catheter does not splint the anastomosis, thus increasing the risk of bladder neck contracture.

Postoperative urethral catheterization is often a source of major discomfort and pain to the patient and may cause more concern to the patient than the procedure itself. Less invasive robotic radical prostatectomy has emerged as a commonly utilized surgical procedure in the management of clinically localized prostate cancer. Patients choosing this procedure are usually driven by its cosmetic benefits, earlier continence, shorter recovery time and minimal blood loss. However, despite the smaller incisions, early ambulation and shorter hospital stay, a few patients, especially the younger ones, continue to complain about the urethral Foley catheter remaining in place for extended time periods. Patients tend to experience urethral discomfort, penile tip pain and meatal encrustation and irritation due to the indwelling catheter. Despite postoperative recovery being essentially uneventful and smooth, patients continue to focus on the catheter and complain—"I wish you did not have to place a urethral catheter . . . "

SUMMARY OF THE INVENTION

It is accordingly an object of the present invention to avoid using a urethral catheter in prostatectomy procedures without compromising the time tested principle of splinting the anastomosis in the initial few days following robotic prostatectomy and the minimization of the potential for complications which can occur following urethral catheterization such as urethral stricture, meatal stenosis, urethritis and ascending urethral bacterial colonization.

It is a further object of the present invention to provide a prostatectomy procedure which provides an alternative to the post surgical catheter which a) splints the anastomosis and prevents the formation of cross synechia and b) drains the bladder, without the need for a tube coming out through the penis.

It is a still further object of the present invention to provide a procedure with improvements over the suprapubic catheter whereby splinting of the anastomosis is effected as well.

In accordance with the present invention the prostatectomy procedure is followed by the placement positioning of a short splinting element such as a small flexible tube with a closed outer end or a solid plug of structural rigidity (hereinafter, referred to collectively as a "splinting tube") across the urethral opening, without significant further extension, in order to splint it open to prevent stricture and bladder neck contracture. The splinting tube, contrary to the normally used urethral catheter, does not permit urine drainage therethrough, but is used in conjunction with a separate drainage tube such as a suprapubic catheter.

The splinting tube is readily placed in position, with minimal steps or traumatization, by a forceps in the bladder during the prostatectomy procedure. The tube is configured to have a larger diameter than the urethral opening to provide a frictional resistance to accidental dislodgement by urinal pressure and is preferably about 30 to 35 mm in length. It is also preferably provided with a diameter comparable to that of the urethral catheter (generally about 5 to 10 mm). It is desirable that the tube or plug have a degree of flexibility for it to conform to the walls of the urethral opening to provide and maintain a snug fit and seal to prevent urine leakage. Placement of the splinting tube or plug requires no trans-urethral movement nor does it require a suprapubic placement procedure. It is desirable that the tube or plug be provided with anchoring means such as a suture connection with the bladder or with the use of integral wing elements at an inner end thereof. These expedients prevent or retard expulsion of the tube or plug as a result of built up urine pressure. The tube or plug is provided with removal means whereby it is removed from the urethral opening after the usual 5-7 day anastomotic healing time. Removal may be effected by utilizing a suture material which dissolves in situ after seven days and/or by the partial or full dissolving of the tube or plug.

The closed or outer end of the tube is preferably connected or tied to a line member which is snaked through the urethra such as by a Foley catheter during other procedures. After the seven days of healing the line member of the splinting tube is externally pulled to disconnect the tube or plug from any anchoring suture and the tube or plug is removed through the urethra. In order to facilitate removal, the tube or plug has an outer diameter no larger than a urethral catheter and is removed in a manner similar to removal of a urethral catheter through the urethra. A line member may not be necessary with self dissolving tubes or plugs which automatically provide the requisite opening in the bladder leading to the urethra.

Generally the present invention comprises a method for facilitating the anastomotic healing of a patient after a radical prostatectomy surgical procedure, without a urethral catheter, comprising the steps of:

a) performing a radical prostatectomy,
b) fixedly positioning a splinting element such, as a closed end tube or solid plug between the urethra and the bladder, across the urethral opening,
c) placement of the splinting element is effected during the performing of the radical prostatectomy and prior to surgical closure, the fixed positioning being effected from a position within the bladder.
d) anchoring the splinting element in position such as by suturing the inner end of the anchor to the interior of the bladder or by use or expanding wing elements,
e) setting a separate urine drainage tube or suprapubic catheter,
f) removing the splinting element after seven days by dissolving or absorption of the suture anchor or deflation of the wing elements and by physical removal of the splinting element through the urethra.

The separate urine drainage tube further contains a valve opening and closing mechanism whereby the valve retains urine within the bladder prior to desired evacuation. The valve further comprises an activation control outside of the body.

The above and other features, advantage of the present invention will become more evident from the following discussion and drawings in which:

SHORT DESCRIPTION OF THE DRAWINGS

FIG. 1 is a schematic cross sectional view of a bladder during a prostatectomy and placement of a splinting tube of the present invention and the position of a separate urine drainage tube, and FIG. 2 is a second embodiment of the splinting tube with anchoring wings.

DETAILED DESCRIPTION OF THE INVENTION AND DRAWINGS

In accordance with the present invention the discomfort, pain and embarrassment of a urethral catheter is effectively eliminated by the combination of a drainage tube or suprapubic catheter commonly utilized for fluid drainage, in combination with a separate splinting element. The splinting element is emplaced with fixed anchoring suturing without additional surgery, during the prostatectomy procedure with forceps already within the bladder for the prostatectomy. Preferably, the drainage tube is positioned at the same time as well.

The material of the splinting element is preferably comprised of an inert material and the connecting sutures which anchor the splinting element to the bladder are of bioabsorbable materials such as used with drug eluting stents, MUSE, and antibiotic coatings used for penile prosthesis. The splinting element is made with structural integrity and the ability to resist stricture forces exerted thereon. The splinting element or tube is dimensioned and positioned to form a liquid tight external seal at the urethral opening and is closed ended to prevent external urinary leakage. The splinting element is preferably comprised of inert flexible materials such as of latex or silicone. Removal of the splinting element is effected by absorption of the anchoring sutures within the body after the seven day healing period. A retrieval line is attached to the tube, preferably to the closed end. At the appropriate time, the line, which is thin and extended through the urethra with minimal discomfort, is pulled to remove the splinting tube from the suturing anchor and to draw it from the urethral opening and through the urethra for full removal.

A hollow, close ended tube is preferred for the splinting element since the hollow can readily retain anchoring knotting of the removing line (which insures that the line does not disengage from the tube during withdrawal of the splinting device). In addition, a hollow tube provides for greater control and minimized. Solid tubes made of appropriate materials may however also be used in the effecting of anastomotic healing. An appropriate tube size is one with a diameter of about 5-10 mm (a bevel gradation in diameter may facilitate initial placement) and a length of about 30-35 mm. Though more difficult to work with than hollow tubes, the solid cylindrical configuration may also be used with appropriate connection of the retrieval line to the solid material. A suturing line to the interior of the bladder is used to anchor the splinting elements from being dislodged as a result of urine pressure. The same urine pressure however eliminates any need for preventing the splinting element from being dislodged inwardly. Alternatively, the splinting element itself may be comprised of a bio-absorbable or dissolving material which results, in time, with automatic self removal, without the necessity of a retrieval line.

In another embodiment a splinting element with wing elements may be used anchor the splinting element in place, with the wings preventing outward dislodgement. The wings are sutured to the inner walls of the bladder, with bio-absorbable sutures.

There are several theoretical advantages of the approach of the present invention including early ambulation and reduced risk of urethral stricture. Use of a conventional urethral catheter is painful during first few days and often moves with the thigh movement. This movement causes more pain at the penis and may possibly be an impediment for early ambulation. All the patients with the catheterless approach of the present invention did not have penile pain and were quite ambulatory following surgery. This early ambulation may pay many dividends in terms of reduced risk for deep vein thrombosis and enhanced overall sense of well being. It was discovered that the most significant benefits included less penile tip and shaft pain and less discomfort in the postoperative period as compared to the standard method. The patients had earlier return to a normal functional status and earlier return to normal activity.

The device in the procedure of the present invention serves two purposes a) to splint the anastomosis and b) to divert urine. In order to avoid the urethral route, several custom made prototypes were tried in human cadaveric experiments which entered the bladder anteriorly and had a distal elongated splint to bridge the anastomosis. The final prototype had a suprapubic drainage tube with a retention mechanism, drainage holes for diverting urine from the bladder and a distal splinting tip to keep the anastomosis patent. This tube was easy to deploy during surgery and to remove after 7 days.

Example

A pilot study was undertaken for the procedure and device of the present invention involving a total of 30 patients (10 subjects and 20 controls), who completed 6 months follow-up.

This was a prospective, non-randomized pilot study to evaluate the feasibility of the urethral catheterless technique in patients undergoing robotic prostatectomy. Over a period of three month, the feasibility of the urethral catheterless approach was tested in 10 patients who specifically requested this modification and signed an informed consent. The data were compared with 20 contemporary patients who did not undergo this modification.

Eligibility criteria—Patients with early prostate cancer who were scheduled to undergo robotic prostatectomy were candidates for this procedure. Patients who had large prostate volumes (>75 cc), median lobe, high body mass index (>30), high risk cancers (Gleason-8, 9 and 10, clinical stage T3 and beyond) and patients with relatively abnormal coagulation parameters were excluded from this pilot study.

Preoperative, intraoperative and postoperative data were collected prospectively. The duration of the catheterization was 7 days in all 30 patients.

The study was used to: 1) evaluate the technique of urethral catheterless robotic radical prostatectomy using this modification, 2) to compare the immediate outcome of the catheterless approach with the standard technique of robotic prostatectomy in terms of discomfort, pain, penile tip irritation, need for urethral catheterization and clot retention, 3) evaluate early urinary continence between two groups and 4) measure the incidence of 6 month bladder neck contracture rates.

Preoperative, intraoperative and postoperative data were collected prospectively. The duration of the catheterization was 7 days in all 30 patients.

Outcomes Measurement:

Demographic, laboratory, oncological, intraoperative and outcomes data were measured and entered in an IRB approved database. Urethral symptoms were recorded using a specifically developed questionnaire. The questionnaire comprised 12 questions pertaining to a) pain at suprapubic site, in penile shaft and penile tip, testicular pain and use of pain medications; b) discomfort while walking and sleeping c) fever; d) erosion/encrustation at tip of penis; e) bladder spasms.

Additional 3$^{rd}$ party telephone interviews were conducted at 10, 14, 21 and 30 days to determine early continence status. Patients were considered continent if they were either using 0 pad or 1 security liner during stressful activities. International Prostate Symptom Scores (IPSS) were obtained preoperatively and at 1, 3 and 6 months postoperatively.

Technique of Robotic Prostatectomy:

All patients underwent the athermal trizonal nerve sparing technique of robotic prostatectomy with total reconstruction of the continence mechanism. The continence preservation technique involves seven key elements: (i) Preservation of the puboprostatic ligaments and arcus tendineus; (ii) Creation of a muscular flap behind the bladder neck (which is later sutured to the distal end of Denonvilliers' fascia behind the sphincter); (iii) Control of the dorsal venous complex using a puboprostatic ligament sparing suture which also provides anterior suspension; (iv) Preparation of a thick and long urethral stump during apical dissection; (v) The 'Pagano principle', reinforcing of the flap behind the bladder neck; (vi) The 'Rocco principle', suturing of the retrotrigonal flap to the distal end of Denonvilliers' fascia, close to the urethral stump, to prevent caudal retraction of the central tendon, thus providing posterior support; and (vii) Re-attachment of the arcus tendineus and puboprostatic plate to the bladder neck after anastomosis is completed.

Technique of Deployment of Device and Anastomosis:

Urethrovesical anastomosis was performed in multiple layers using two 3-0 monocryl sutures on a RB needle. Once the two posterior layers of anastomosis were completed, (Rocco stitch followed by posterior bladder) the device was introduced through a suprapubic puncture made under direct vision and entered the bladder 2-3 inches proximal to the bladder neck and advanced the distal attached tip of the device through the anastomosis. It took 2-3 minutes to complete this phase of the surgery and the anterior anastomosis was completed in two layers (bladder followed by reconstruction of the puboprostatic-arcus tendineus complex).

Post Operative Care:

On the 7$^{th}$ day, the suprapubic device was removed following a cystogram. The degree of pain, discomfort and bother were assessed by a self administered questionnaire.

Statistical Analysis:

The data were entered into an Excel spreadsheet and the chi-square test and Student t test were applied to compare the group characteristics as well as the incidence of complications between the groups, with critical values and statistical significance at $P<0.05$.

Results:

Group 1 was the study group of 10 patients in whom robotic radical prostatectomy was performed using catheter less approach. Group 2 comprised of 20 age, tumor stage, and prostate volume matched patients undergoing the conventional urethral catheterization technique performed in same time period. The two groups were also comparable in terms of console times, amount of bleeding, or volume of blood transfusion (0), anastomotic leakage (0) and post operative retention rates (0) ($P>0.05$). In Group 1 which was the study group of 10 subjects, we used a custom made suprapubic catheter which provided a small anastomotic splint, two balloons to prevent either upward or downward migration, multiple holes for drainage and the ability to retract the splint to give a voiding trial before removing the drainage device. Group 2 was the control group of 20 patients in whom standard urethral catheterization was performed with an 18F Silastic Foley catheter. Demographic, intraoperative and outcomes data were measured and entered in an IRB approved database. Urethral symptoms were recorded using a specially developed questionnaire.

These values are shown in Table 1.

TABLE 1

Baseline, intraoperative and post operative outcomes in two matched cohorts

| | MEAN (RANGE) | | |
|---|---|---|---|
| VARIABLES | GROUP 1 (N = 10) CATHETER LESS | GROUP 2 (N = 20) URETHRAL CATHETER COHORT | P VALUE |
| BASELINE PARAMETERS | | | |
| AGE | 60.76 (52.8-67.3) | 59.99 (55.8-66.3) | NS |
| BMI | 26.10 (22.9-33.2) | 27.25 (23.08-34.16) | NS |
| Serum (PSA) ng/ml | 4.2 (2-6.8) | 5.5 (3.2-12.1) | NS |
| IPSS | | | |
| Prostate Volume ml | | | |

TABLE 1-continued

Baseline, intraoperative and post operative outcomes in two matched cohorts

| | MEAN (RANGE) | | |
|---|---|---|---|
| VARIABLES | GROUP 1 (N = 10) CATHETER LESS | GROUP 2 (N = 20) URETHRAL CATHETER COHORT | P VALUE |
| Biopsy Gleason score | | | NS |
| 2-6 | 8 | 8 | |
| 7 (3 + 4) | 2 | 2 | |
| 7 (4 + 3) | — | — | |
| 8-10 | — | — | |
| Clinical stage | | | NS |
| T1b | — | — | |
| T1c | 9 | 9 | |
| T2a | 1 | 1 | |
| T2b | | | |
| T3 | | | |
| INTRA-OPERATIVE PARAMETERS | | | NS |
| Estimated Blood loss (cc) | 170 | 155 | NS |
| Console time in minutes | 80 (52-108) | 78 (46-110) | NS |
| Extra time for procedure (minutes) | 3 (2-5) | — | NS |
| Intraoperative blood transfusion | Nil | Nil | NS |
| POST OPERATIVE PARAMETERS | | | NS |
| Pathological Stage | | | NS |
| T2a | 1 | 2 | |
| T2b | 1 | — | |
| T2c | 7 | 8 | |
| T3a | 1 | — | |
| Duration of catheterization or device removal (days) | 7 | 7 | NS |
| Clinical urinary leak | Nil | Nil | NS |
| Post operative retention | Nil | Nil | NS |
| Bladder neck contracture | Nil | Nil | NS |

As is seen in the table 2, most patients achieved continence in 6-12 weeks. The catheter-less group had a greater percentage of patients who became continent almost immediately, however this was not statistically significant (50% v/s 20% p=0.09).

TABLE 2

Continence outcomes in two cohorts of patients (0 pad status)

| Zero pad status | Group 1 N = 10 | Group 2 N = 20 | P value |
|---|---|---|---|
| Continence within 1 week | 6 (50%) | 4 (20%) | <0.5 |
| Continence within 6 weeks | 10 (100%) | 16 (80%) | NS |
| Continence within 12 weeks | 10 (100%) | 18 (98%) | NS |

Table 3 summarizes data regarding pain, discomfort and early ambulation. No patient in group 1 had pain in penile shaft or tip as compared to 18/20 patients in group 2. (p<0.05)). 2 patients in group 1 complained of minimal pain at the suprapubic puncture site. 2 patients in group 1 had discomfort walking and sleeping as compared to 14 patients in group 2 (p<0.05) and 3 patients in group 1 had bladder spasms compared to 8 patients in group 2. No patient either group had hematuria or clot retention requiring irrigation. No patient in either group had symptoms suggestive of a bladder neck contracture at 6 months follow-up.

TABLE 3

Pain and discomfort outcomes

| | Group 1 n = 10 | Group 2 n = 20 | P value |
|---|---|---|---|
| Pain at site of Suprapubic catheter or penile shaft | 2 | 18 | <0.5 |
| Pain at tip of penis | 0 | 10 | <0.5 |
| Erosion at penile tip | 0 | 5 | <0.5 |
| Discomfort walking and sleeping | 2 | 14 | <0.5 |

CONCLUSIONS

Urethral catheterless robotic radical prostatectomy is feasible. The advantages are decreased penile shaft and tip pain and decreased patient discomfort and an earlier return of continence. In this pilot study there was no late term complication such as bladder neck contracture.

Results:

The two groups were comparable in terms of age, serum prostate specific antigen (PSA) values, body mass index (BMI), Gleason scores, tumor stage, operating time, amount of bleeding, console times, anastomotic leakage and post operative retention rates. The study group had significantly less penile shaft or tip pain and discomfort during walking or sleeping. No patient in either group had hematuria or clot retention requiring irrigation.

With reference to the drawings, In FIG. 1, the interior of bladder 10, is shown during a robotic prostatectomy procedure. Laparoscopically inserted forceps 20 carry and position splinting element 30, shown as a tube formed of medical grade latex with a closed forward end 30a and a removal string 31 sutured to the forward end 30a. The inner or distal end 30b (or an extension thereof as shown) is provided with suture material 32. Forceps 20 position the splinting element 30 across the anatomotic opening 11 between the bladder 10 and the urethra 12.

The removal string 31 is snaked through the urethra for external access when necessary for removal of the splinting tube. During surgery a Foley catheter is placed through the urethra 12 to assist in anastomosis. At the end, before anastomotic stitches are tied, the Foley catheter is pulled outside through the anterior gap in anastomosis and string 31 is tied through the tip of the Foley catheter. The Foley catheter is pulled out (with string) and the string then protrudes outside the urethra. Splinting element 30 is positioned across the anastomosis and is secured using a 4-O Chromic catgut to the bladder wall (which dissolves over net few days). Anastomosis is closed once a suprapubic catheter 40 is properly positioned.

Suture material 32 is sutured to an internal wall of the bladder to anchor the splinting element 30, once positioned. The separate suprapubic drainage cathether 40 is positioned through a wall of the bladder 10 for urine drainage.

The splinting element with integral anchoring members is shown in FIG. 2. The splinting element 33 is provided with wing elements 34a and 34b which are used with the suture material 32. The wing elements 34a and 34b engage the bladder wall, peripheral to the bladder opening to provide an anchor for the splinting element 33. The splinting element 33 is removed by the dissolving of the sutures holding the wing element 34a and 34b and by pulling the splinting element through the urethra with the string 31 as in the first embodiment. Alternatively, splinting elements 30 and 33 may be comprised of a self dissolving material whereby the bladder "plug" is automatically opened over time without need for a retrieval line or string. It is however preferred, for ensuring removal, that the splinting element be provided with externally accessible retrieval means such as string 31.

It is understood that the above Example and description of the preferred embodiment are exemplary of the present invention and that changes in material, components, structure, method steps and the like may be made without departing from the scope of the present invention as defined in the following claims.

What is claimed is:

1. A method for facilitating the anastomotic healing of a patient after a radical prostatectomy surgical procedure, without a urethral catheter, comprising the steps of:
   a) performing a radical prostatectomy,
   b) positioning a splinting element across a urethral opening between a urethra and bladder of the patient,
   wherein the splinting element is positioned from a position within the bladder during the radical prostatectomy and prior to surgical closure,
   c) anchoring the splinting element in position relative to the interior of the bladder,
   d) setting a urine drainage tube for urine drainage from the bladder, wherein the urine drainage tube is separate from the splinting element and
   e) removing the splinting element after anastomotic healing.

2. The method of claim 1 wherein the splinting element is comprised of a bio-absorbable material which dissolves to effect the step of removing the splinting element after anastomotic healing.

3. The method of claim 1 wherein the splinting element is provided with a retrieval member which is accessibly placed external to the body of the patient for the step of removing the splinting element after anasomotic healing by pulling the splinting element through and out of the urethra.

4. The method of claim 3, wherein the retrieval member comprises a string affixed to the splinting element and wherein the string is positioned to extend through and out of the urethra.

5. The method of claim 1, wherein the splinting element is configured with a diameter between 5 to 10 mm.

6. The method of claim 5, wherein the splinting element is configured with a length of between 30 to 35 mm.

7. The method of claim 1, wherein the splinting element is anchored into a fixed position by suturing the splinting element to the inner wall of the bladder adjacent the urethral opening.

8. The method of claim 7 wherein a bio-absorbable suture material is used in suturing the splinting element to the bladder and the suture material dissolves after anastomotic healing.

9. The method of claim 8, wherein the splinting element is integrally provided with a foldable wing element having an extended diameter greater than the urethral opening, the wing element providing an anchoring engagement between the wing element and the bladder peripheral to the urethral opening, the wing element being sutured to the inner wall of the bladder for the anchoring engagement.

10. The method of claim 1, wherein the separate urine drainage tube is configured as a suprapubic catheter with a valve control for control of urine drainage.

\* \* \* \* \*